United States Patent [19]

Balton et al.

[11] Patent Number: 5,574,214
[45] Date of Patent: Nov. 12, 1996

[54] APPARATUS FOR DRYING DIELECTRIC OIL

[75] Inventors: Christopher S. Balton, Manitou Springs; James D. Pierce, Colorado Springs; Gregory S. Sprenger, Colorado Springs; Benjamin G. Taylor, Colorado Springs, all of Colo.

[73] Assignee: Velcon Filters, Inc., Colorado Springs, Colo.

[21] Appl. No.: 443,108

[22] Filed: May 17, 1995

[51] Int. Cl.⁶ .......................... G01N 37/00; G01N 33/26
[52] U.S. Cl. .................. 73/61.43; 73/61.61; 324/698; 210/689
[58] Field of Search .................. 73/61.43, 61.41, 73/61.44, 61.59, 61.61, 64.56, 863.23, 53.05, 334.04; 324/698, 696, 694; 210/689

[56] References Cited

U.S. PATENT DOCUMENTS

| | | | |
|---|---|---|---|
| 2,752,586 | 6/1956 | Jordan | 73/61.43 |
| 2,767,574 | 10/1956 | Schurch | 73/61.43 |
| 2,943,594 | 7/1960 | Price | 73/61.61 |
| 3,238,452 | 3/1966 | Schmitt et al. | 73/61.43 |
| 3,257,842 | 6/1966 | Lerner | 73/61.43 |
| 3,398,208 | 2/1968 | Ward . | |
| 4,019,977 | 6/1977 | Hachadoorian . | |
| 4,129,501 | 12/1978 | Haynes | 210/689 |
| 5,271,842 | 12/1993 | Degen et al. | 210/689 |

Primary Examiner—Hezron E. Williams
Assistant Examiner—Nashmiya Ashraf
Attorney, Agent, or Firm—Donald R. Fraser

[57] ABSTRACT

Apparatus for removing water from a dielectric oil includes first and second spaced-apart electrically conductive walls, a bed of molecular sieves between the first and second walls, and a device for measuring the capacitance across the bed of molecular sieves between the first and second walls.

6 Claims, 3 Drawing Sheets

APPARATUS FOR DRYING DIELECTRIC OIL

FIELD OF THE INVENTION

This invention relates generally to apparatus for drying dielectric oils. More particularly, the invention is directed to apparatus containing molecular sieves to remove water from dielectric oils used in transformers and electrical cables, in association with means for monitoring the molecular sieves' ability to dry the dielectric oils.

BACKGROUND OF THE INVENTION

Electrical power transformers and transmission cables generally contain a dielectric insulating oil to prevent shorting of the electrical potential within the device. It is important that these oils contain very little free or dissolved water. Generally, dielectric oils must contain no more than about ten parts per million water.

Transformers are periodically serviced by heating the dielectric oil above about 200° F. under a high vacuum to remove built-up dissolved water. This is generally accomplished by circulating the oil through a heating and evacuation system mounted on a mobile service truck. This process is quite expensive, requiring special expertise to operate the equipment and additional manpower to set up and then disconnect the mobile system.

Moreover, new transformer and cable dielectric oils generally contain more than 10 ppm water, and must be dried before being injected into such electrical equipment. Heating/evacuating systems typically are used to dry these new dielectric oils as well.

U.S. Pat. No. 4,019,977 to Hachadoorian et al. discloses a demister-coalescer for removing water from oil. The oil containing dissolved water is passed through a vessel containing a dispersing material. The vessel is maintained under a vacuum, and water vapor is removed from the oil.

U.S. Pat. No. 3,398,208 to Ward discloses the use of a molecular sieve bed for drying a stream of hydrocarbon-containing water. The wet hydrocarbon is passed through the bed where the water is absorbed into the pores of the molecular sieve. When the molecular sieve bed becomes saturated with water, and retained water is detected in the effluent hydrocarbon stream, the bed is then taken out of service and regenerated in a conventional manner to remove the absorbed water.

It would be desirable to develop apparatus for drying dielectric oils in a manner that does not require the downtime and expense of the conventional heating/evacuating systems, and which can consistently and reliably reduce the dissolved water content of the oils to a value below about 10 ppm.

SUMMARY OF THE INVENTION

Accordant with the present invention, apparatus for drying, i.e., removing water from a dielectric oil has surprisingly been discovered, comprising: a first electrically conductive wall; a second electrically conductive wall; a bed of molecular sieves between the first and second walls; and means electrically connected to the first and second walls for measuring the capacitance across the bed between the first and second walls.

The inventive apparatus for drying a dielectric oil according to the present invention is particularly useful for removing water from transformer and cable dielectric oils.

BRIEF DESCRIPTION OF THE DRAWINGS

Further objects and advantages of this invention will be apparent from the following description and appended claims, reference being made to the accompanying drawings forming a part of the specification, wherein like reference characters designate corresponding parts in the several views.

DETAILED DESCRIPTION OF THE PREFERRED EMBODIMENTS

Figure 1:
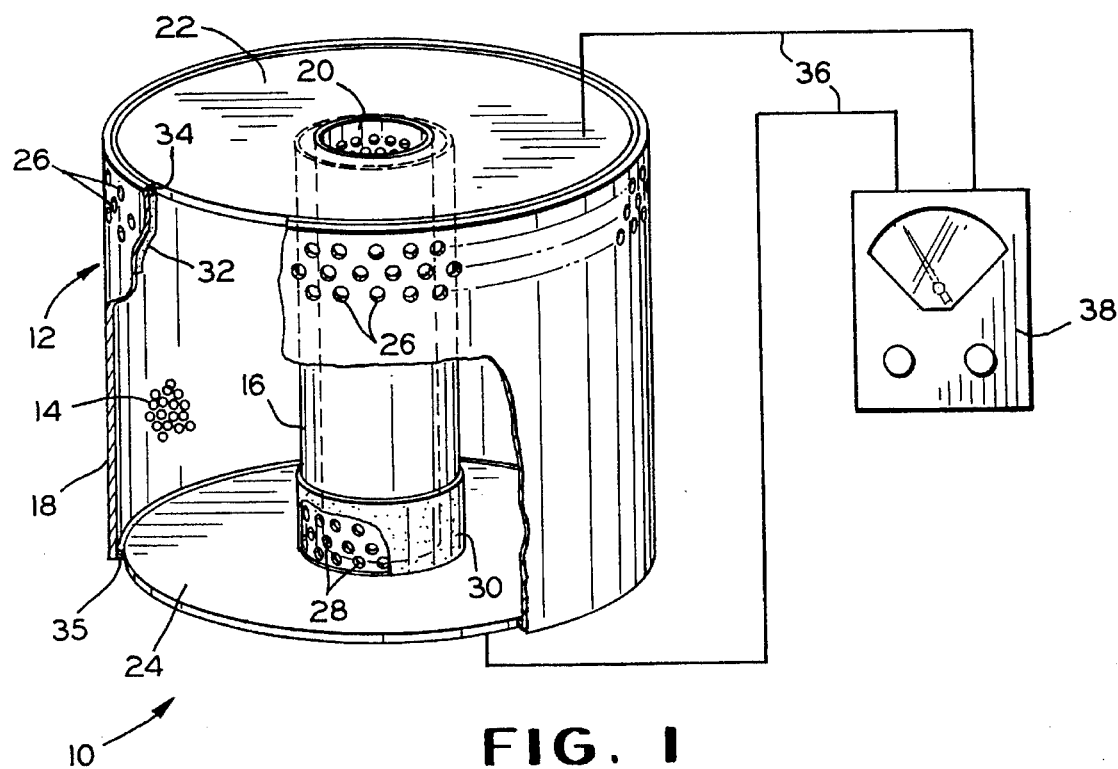
FIG. 1 is a diagrammatic perspective view, partially cut-away, of a device containing a bed of molecular sieves, electrically connected to means for measuring the capacitance across the bed between two of the walls of the device, according to the present invention.
Figure 3:
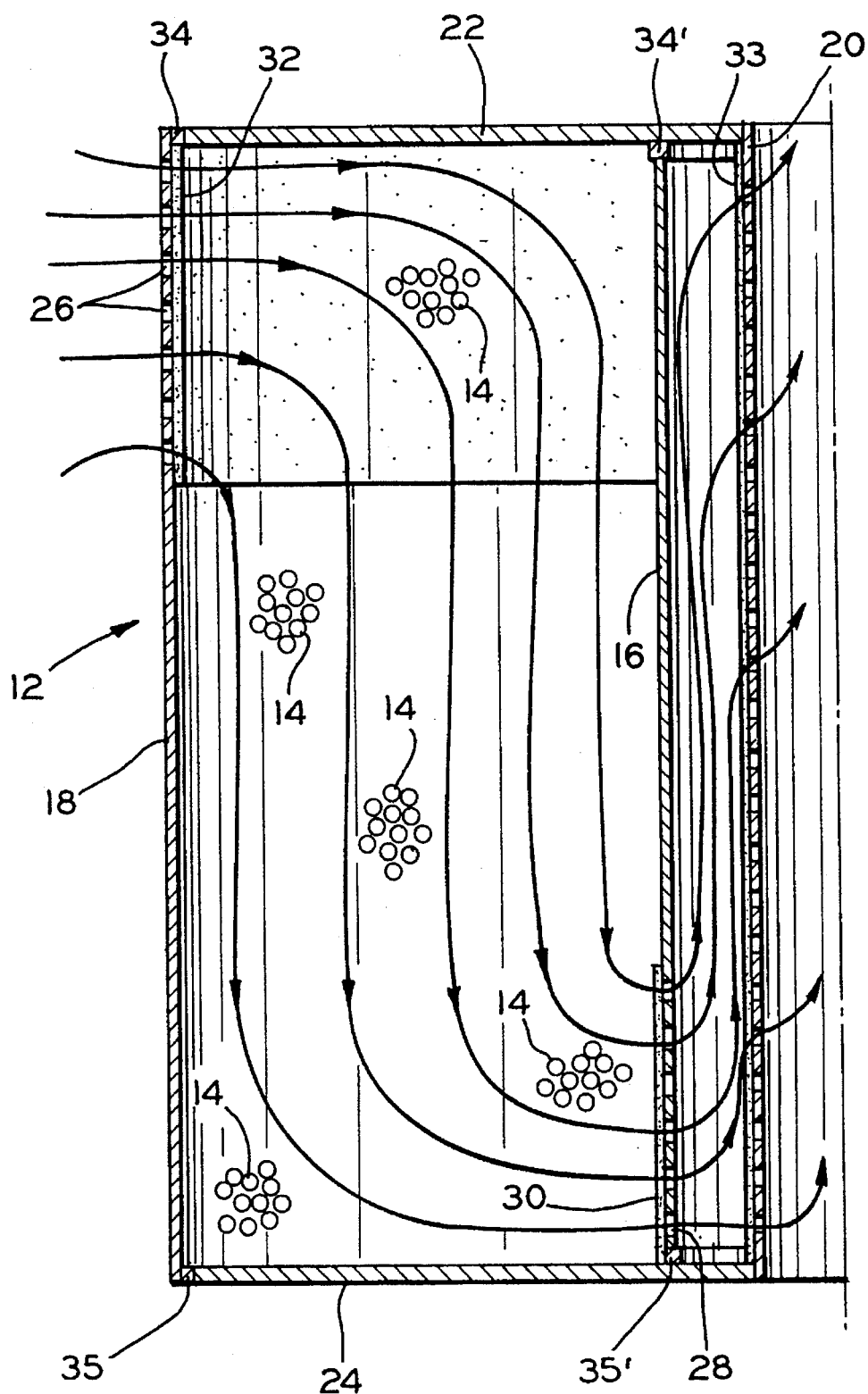
FIG. 3 is a diagrammatic illustration of the fluid flow through the device illustrated in FIG. 1.

Referring now to FIGS. 1 and 3, there is shown generally at 10 apparatus for removing water from a dielectric oil, according to the present invention. The apparatus 10 typically comprises a cartridge 12 for containing a bed 14 of molecular sieves. The bed 14 of molecular sieves is represented by the particles illustrated in FIG. 1, and in actuality fills the entire interior of the cartridge between the inner surface of an outer tube 18 and the outer surface of a middle tube 16.

The cartridge 12 includes the inner cylindrical middle wall or tube 16, and the outer coaxial cylindrical wall or tube 18, a perforated inner tube 20, and top and bottom end caps or walls 22 and 24, respectively. The outer tube 18, the middle tube 16, the top wall 22, and the bottom wall 24 define an enclosed annular chamber for mainlining the bed 14 of molecular sieves. The outer cylindrical tube 18 includes a plurality of apertures 26 located around the periphery thereof adjacent its intersection with the top wall 22. The middle cylindrical wall 16 includes a plurality of outlet apertures 28 located around the periphery thereof adjacent its intersection with the bottom wall 24. A strip 30 of porous material is adhesively positioned and secured on the outer surface of the middle tube 16 over the outlet apertures 28 inside the chamber containing the bed 14 of molecular sieves. Similarly, a strip 32 of porous material is adhesively positioned and secured on the inner surface of the outer tube 18 adjacent the inlet apertures 26.

The apertures 26 and 28 in the middle and outer cylindrical tubes 18 and 16, respectively, allow the dielectric oil to flow through the bed 14 of molecular sieves within the cartridge 12. The apertures 28 and 26 are positioned at spaced-apart parallel planes which are perpendicular to the axis of the coaxial middle and outer tubes 16 and 18, respectively.

As clearly illustrated in FIG. 3, the dielectric oil flowing into the bed 14 of molecular sieves from the outside of the cartridge 12 through the apertures 26 in the outer tube 18 then flows through the bed 14 initially in a direction normal to longitudinally axis of the cartridge 12 and thence substantially parallel to the axis of the coaxial middle and outer tubes 16 and 18, respectively, thereafter exit the bed 14 through apertures 26 in the middle tube 16.

Thereafter, the treated dielectric oil is caused to enter the zone between the middle tube 16 and the perforated or apertured inner tube 20. The outer surface of the inner tube 20 is covered with a filter paper material 33 which functions to militate against the passage therethrough of any particulate material which may occur from fractured pieces of the molecular sieves which may have occurred in transit, for example.

The resultant columnar flow of the transient oil tends to produce an efficient contact between the oil and the major portion of the molecular sieves contained within the cartridge 12. Prior to exiting the bed 14 through the apertures 28 of the middle tube 16, the dielectric oil passes through the porous material 30 which functions to ready permit the flow of dielectric oil, and simultaneously prohibits the escape of the molecular sieves of the bed 14. The strips 30 and 32 of porous material may be made from any conventional material such as, for example, felt cloth, fiber glass mesh, and the like which are effective to militate against the passage therethrough of the molecular sieves.

FIG. 1 illustrates that the cartridge 12 may conveniently be formed in a cylindrical shape, so that it may easily be inserted and withdrawn from a conventional filter housing such as is typically used to hold particulate filters used in the conventional processing of dielectric oils.

The top and bottom end caps 22 and 24, respectively, of the cartridge 12 illustrated in FIGS. 1 and 3 are typically formed from an electrically conductive material, e.g., steel, aluminum, copper, etc., as well as alloys thereof. The end caps 22 and 24 are electrically insulated from the outer tube 18 by insulator ring members 34 and 35, respectively, and from the middle tube 16 by insulator ring members 34' and 35', respectively. The end caps 22 and 24 are electrically connected to means for measuring the capacitance across the bed 14 by electrically conductive wires 36 which in turn are connected to a conventional capacitance meter 38.

Figure 2:
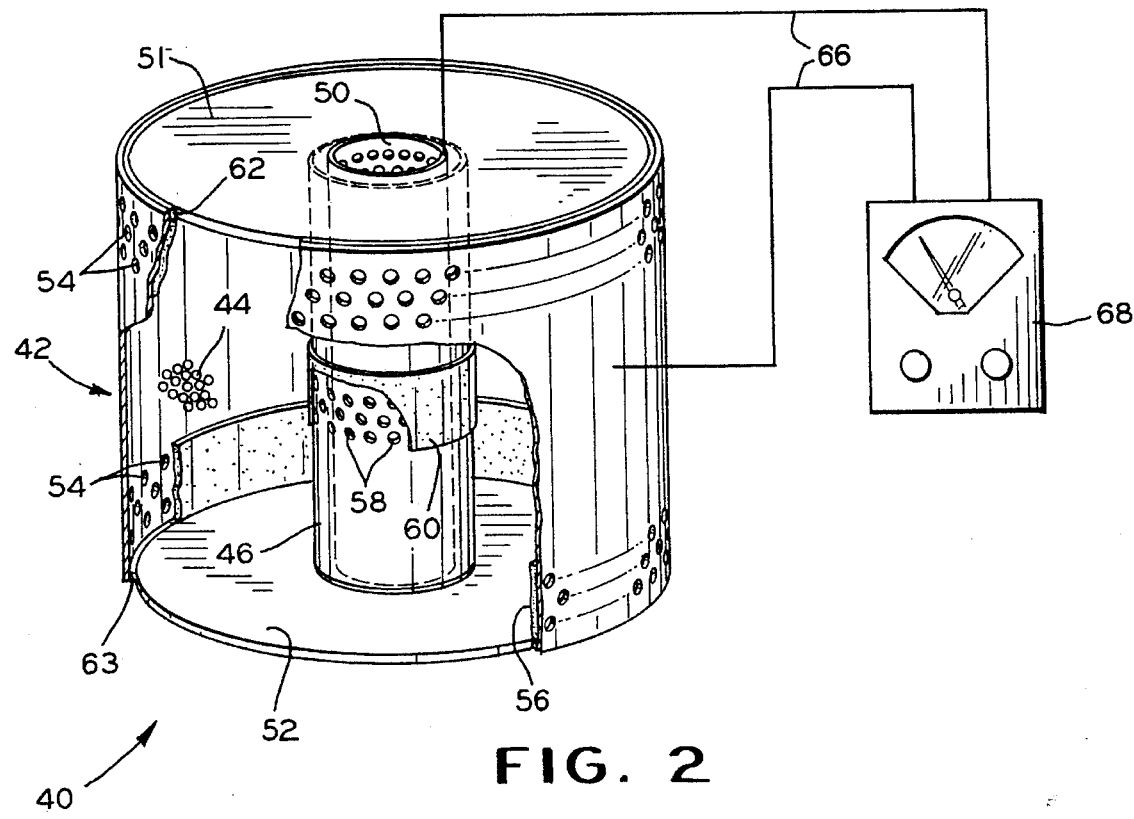
FIG. 2 is a diagrammatic perspective view, partially cut-away, of a device similar to the device illustrated in FIG. 1, also containing a bed of molecular sieves, and also electrically connected to means for measuring the capacitance across the bed between two of the walls of the device.
Figure 4:
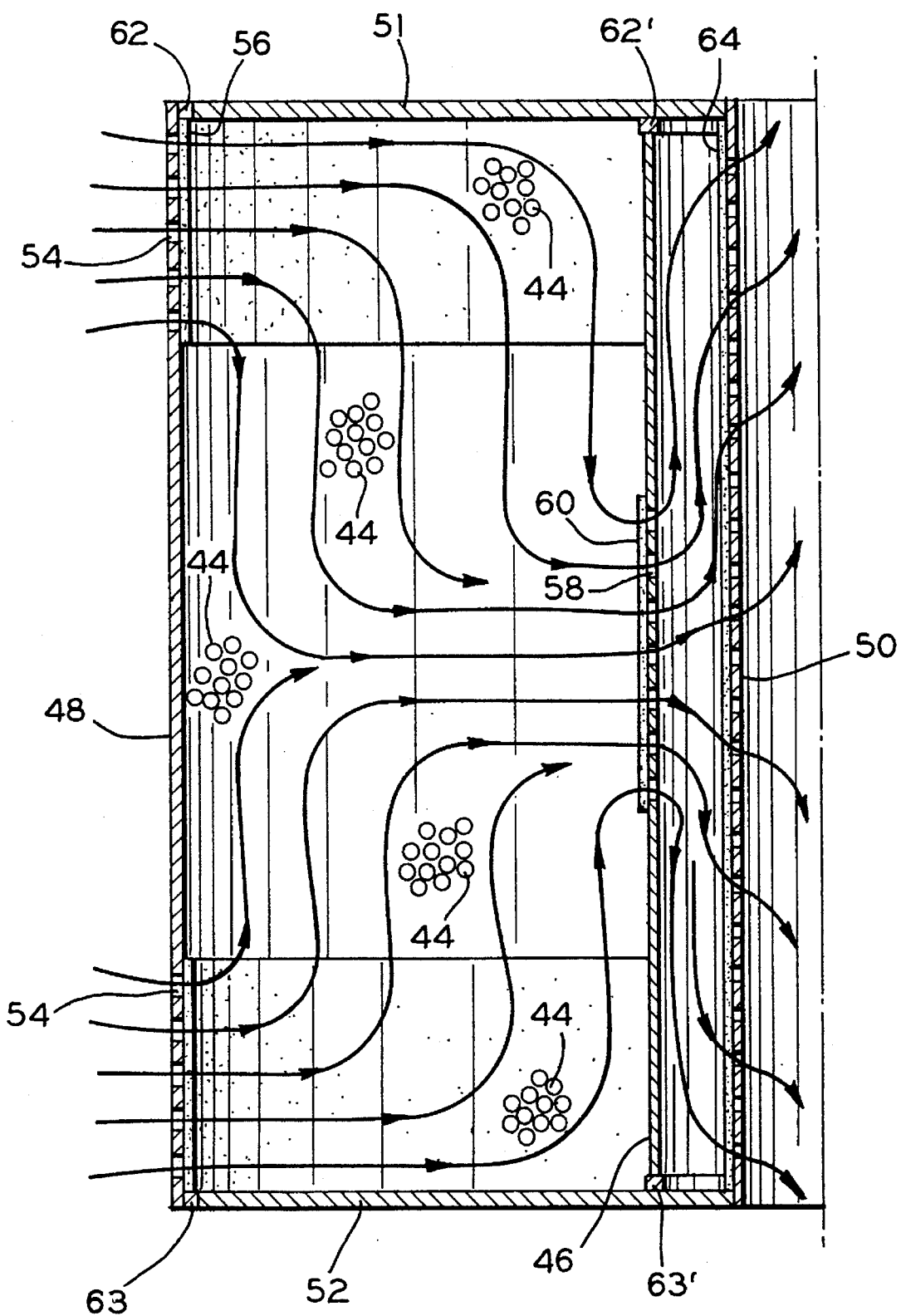
FIG. 4 is a diagrammatic illustration of the fluid flow through the device illustrated in FIG. 2.

FIGS. 2 and 4 illustrate another embodiment of apparatus 40 for removing water from a dielectric oil, according to the present invention. The apparatus 40 includes a cartridge 42 for containing a bed 44 of molecular sieves within an annular space defined by a middle cylindrical tube 46, an outer coaxial cylindrical tube 48, a perforated inner tube 50 and cooperating top and bottom end caps 51 and 52, respectively. The dielectric oil to be dried is passed through two spaced apart sets of apertures 54 in the outer cylindrical tube 48, inwardly through associated strips 56 of porous material adhesively positioned and secured to the inner surface of the outer tube 48, and then through the bed 44. After passage through the bed 44, the treated dielectric oil is caused to pass outwardly through a plurality of apertures 58 formed in the inner cylindrical tube 46 and a strip 60 of porous material adhesively positioned and received to the outer Surface of the middle tube 46 over the aperture 58.

Thereafter, the treated dielectric oil is caused to enter the zone between the middle tube 46 and the apertured inner tube 50. The outer surface of the inner tube 50 is covered with a filter paper material 64 which functions to militate against the passage therethrough of any particulate material which may occur from fractured pieces of the molecular sieves which may have taken place during the shipment of the cartridge, for example.

As will be readily apparent to one ordinarily skilled in the art, due to the placement of the apertures 54 and 58 in the outer and middle coaxial cylindrical tubes 48 and 46, respectively, the flow of dielectric oil through the bed 44 is caused to travel substantially parallel to the axis of the coaxial tubes 46 and 48, throughout most of the volume of the bed 44. The paths of travel of the dielectric oil being treated are particularly manifest in FIG. 4.

The middle and outer cylindrical tubes 46 and respectively, are typically formed from an electrically conductive material and are electrically insulated from one another and the top end cap 51 and bottom end cap 52 by sealing insulators 62, 62', 63 and 63'. A conventional capacitance meter 68 is electrically coupled to middle tube 46 and to the outer tube 48 by electrical conductive wires 66. The meter 68 is capable of measuring the capacitance across the bed 44.

Conveniently, the flow of the dielectric oil to be dried by the apparatus of the present invention is substantially parallel to the axis of the coaxial middle and outer cylindrical tubes 46 and 48, which maintains the flow velocity of the dielectric oil through the bulk of the molecular sieves of the bed 44 at a substantially constant rate. If the flow were directed from the outer cylindrical tube 48 radially inwardly to the middle cylindrical tube 46, the flow of dielectric oil would accelerate thereby reducing the efficiency of water removal from the dielectric oil being treated.

The axial length of the bed 44 of the molecular sieves and flow velocity of the dielectric oil have an important impact upon the water removal efficiency. An increase dielectric oil flow velocity reduces the ability of the molecular sieves to remove free and dissolved water; and a bed having a shortened axial length reduces the water removal performance and service life of the cartridge containing molecular sieves.

The molecular sieves useful in the present invention are commercially available. They are typically crystalline aluminosilicates of Group I A and Group II A elements such as, for example, sodium, potassium, magnesium, calcium, and the like. Structurally, molecular sieve zeolites are complex crystalline inorganic polymers based upon an infinitely extending framework of $AlO_4$ and $SiO_4$ tetrahedra linked to each other by the sharing of oxygen ions. These framework structures contain channels or interconnected voids that are occupied by the cations and water molecules. In producing molecular sieves used for removing water, a crystalline host structure permeated by micropores remains intact which may amount to 50% of the crystalline structure by volume.

Molecular sieves found to be particularly useful according to the present invention include those commercially designated as 3A, 4A, 5A, and 13X. These designations indicate the pore diameter in angstroms, and generally indicate the size of the molecules that can be adsorbed into the interstices of the molecular sieve particles. The molecular size of water is less than about 3 angstroms, and so it can be adsorbed by any of the aforementioned molecular sieve grades. Larger molecules are not adsorbed if their size is greater than the interstices. The particle size of the molecular sieves conveniently can range from powders a few micrometers in diameter up to granules one-eighth inch in diameter. Preferred molecular sieves according to the present invention are classified as 14×30 mesh, indicating that the particles will pass through a 14 mesh screen but will be retained by a 30 mesh screen. Preferred molecular sieves bearing the product designation MOLSIV ADSORBENT Type 4A may be obtained from Molecular Sieve Adsorbents of Des Plaines, Ill.

Molecular sieves generally contain fine dust particles along with the primary granules. Dielectric oil flowing through the molecular sieves can dislodge these dust particles. The filter material 33 of the embodiment illustrated in FIGS. 1 and 3, and 64 of the embodiment illustrated in FIGS. 2 and 4 surrounding the apertures in the inner cylindrical tubes 20 and 50, respectively, is selected to provide filtering capability for capturing these dust particles without adding a significant restriction to the flow of dielectric oil.

An inherent problem associated with the use of molecular sieves for removing water from a flowing stream of dielectric oil is that there is no convenient way to determine when the bed is about to become saturated with water. In the prior art, the effluent stream was monitored for water content; and when the water content of the effluent stream began to rise, the saturated bed of molecular sieves was taken out of service. This is an unacceptable method, however, for determining when to replace a molecular sieves bed used to dry dielectric oils used in transformers and electrical cables, in which the water content cannot exceed about 10 ppm.

The present invention employs means for measuring the capacitance across the bed of molecular sieves between the electrically conductive walls. The electrically conductive walls of the respective cartridges act as the electrodes of a capacitor, with the molecular sieves adsorbed water, and oil acting as the dielectric media therebetween. The dielectric constant of a capacitor is related to its geometry, size, and the nature of the dielectric material between the electrodes. Higher dielectric constants enable a capacitor to store more energy. The dielectric constant in the present invention is the ratio of the capacitance of the bed of molecular sieves, adsorbed water, and dielectric oil compared to the capacitance between the electrically conductive walls with a vacuum as the dielectric material. The dielectric constant of molecular sieves is about 4, while the dielectric constants of a typical dielectric oil and water are about 2.5 and 78, respectively. The substantially higher value for water is sufficient to affect the capacitance of the container of the present invention, even in relatively small quantities.

The capacitance across the bed of molecular sieves may be measured by conventional means, such as, for example, a capacitance meter bearing the product designation Model 820 which may be obtained from Dynascan Corporation of Chicago, Ill. In operation, the capacitance is measured continuously or periodically as dielectric oil is flowing through the bed and water is being adsorbed onto the molecular sieves. The capacitance is low when no water is adsorbed onto the molecular sieves. The capacitance increases as water is adsorbed onto the molecular sieves and the amount of water retained in the effluent stream rises. Ultimately, an upper limit capacitance value is measured across the bed of molecular sieves when the water content of the effluent stream of dielectric oil rises to about 10 ppm. As will readily be apparent to one ordinarily skilled in the art, the empirical relationship between capacitance and dielectric oil effluent stream water content may easily be obtained by no more than routine experimentation. When the upper limit capacitance value is reached, indicating that the water content of the effluent stream of dielectric oil is about to exceed 10 ppm, then the container of molecular sieves is removed from its housing and replaced with a fresh one.

Common dielectric oils are generally aliphatic mineral oils consisting of complex mixtures of straight and branched-chain compounds and cyclic structures. Often these dielectric oils also comprise sizable aromatic contents consisting primarily of benzene and naphthalene derivatives.

From the foregoing description, one ordinarily skilled in the art can easily ascertain the essential characteristics of this invention and, without departing from its spirit or scope, can make various changes and modifications to adapt the invention to various uses and conditions.

In accordance with the provisions of the patent statutes, the present invention has been described in what is considered to represent its preferred embodiment. However, it should be understood that the invention can be practiced otherwise than as specifically illustrated and described without departing from its spirit or scope.

What is claimed is:

1. Apparatus for measuring and removing water from a dielectric oil, comprising:

a first cylindrical wall, including a plurality of apertures located around the periphery of said first cylindrical wall;

a second cylindrical wall, coaxial with said first cylindrical wall said second cylindrical wall including a plurality of apertures located around the periphery of said second cylindrical wall, the apertures in said first and second cylindrical walls forming spaced-apart parallel planes perpendicular to the axis of said first and second cylindrical walls;

a first annular electrically conductive wall, perpendicular to the axis of and affixed to said first and second cylindrical walls;

a second annular electrically conductive wall, said second annular wall being affixed to the first and second cylindrical walls and parallel and spaced-apart relative to said first annular wall;

a bed of molecular sieves between said first and second annular walls; and means electronically connected to said first and second annular walls for measuring the capacitance across the bed between Said first and second annular walls to determine the water content of a dielectric oil between said first and second annular walls.

2. The apparatus for removing water from a dielectric oil according to claim 1, wherein the first and second cylindrical walls are metal.

3. The apparatus for measuring and removing water from a dielectric oil according to claim 1, wherein the molecular sieves are selected from the group consisting of 3A, 4A, 5A, and 13X molecular sieves, and mixtures thereof.

4. The apparatus for measuring and removing water from a dielectric oil according to claim 1, wherein the molecular sieves comprise 14×30 mesh molecular sieves.

5. The apparatus for measuring and removing water from a dielectric oil according to claim 1, wherein the means for measuring the capacitance comprises a capacitance meter.

6. The apparatus for measuring and removing water from a dielectric oil according to claim 1, further comprising layers of filter material disposed around the periphery of each of said first and second cylindrical walls covering the apertures therein to prevent the migration of molecular sieves from the bed through the apertures.

* * * * *